United States Patent [19]

Drake

[11] Patent Number: 4,599,456

[45] Date of Patent: Jul. 8, 1986

[54] NOVEL ALDEHYDE-PHOSPHINE COMPOSITIONS AND USES THEREFOR

[75] Inventor: Charles A. Drake, Nowata, Okla.

[73] Assignee: Phillips Petroleum Company, Bartlesville, Okla.

[21] Appl. No.: 684,210

[22] Filed: Dec. 20, 1984

[51] Int. Cl.[4] ............................................. C07C 47/058
[52] U.S. Cl. ......................................... 568/421; 568/6; 568/62; 568/422; 568/449; 568/492; 252/400 A
[58] Field of Search ................... 252/400 A; 568/441, 568/449, 458, 878, 454, 492, 421, 427, 438, 854, 868, 913; 210/909, 749; 203/6, 57, 58, 62, 63

[56] References Cited

U.S. PATENT DOCUMENTS

| | | | |
|---|---|---|---|
| 2,874,100 | 2/1959 | Breler et al. | 568/421 |
| 3,878,250 | 4/1975 | Sato | 568/421 |
| 3,981,925 | 9/1976 | Schwager et al. | 568/454 |
| 4,190,729 | 2/1980 | Forster | 203/6 |
| 4,258,214 | 3/1981 | Bahrmann et al. | 568/454 |
| 4,277,627 | 7/1981 | Bryant et al. | 568/454 |
| 4,283,304 | 8/1981 | Bryant et al. | 568/454 |
| 4,292,448 | 9/1981 | Tsunoda et al. | 568/454 |
| 4,334,042 | 6/1982 | Matsumoto et al. | 203/6 |
| 4,400,547 | 8/1983 | Dawes et al. | 568/454 |
| 4,404,185 | 9/1983 | Maccone et al. | 424/84 |
| 4,414,419 | 11/1983 | Weber et al. | 568/421 |
| 4,451,679 | 5/1984 | Knifton et al. | 568/909 |

FOREIGN PATENT DOCUMENTS

| | | | |
|---|---|---|---|
| 156528 | 9/1982 | Fed. Rep. of Germany | 568/492 |
| 13009 | 3/1971 | Japan | 568/421 |
| 0142231 | 11/1981 | Japan | 568/421 |

OTHER PUBLICATIONS

Dawes et al., "Chemical Abstracts" vol. 99(19) 157836u.

*Primary Examiner*—Werren B. Lone
*Attorney, Agent, or Firm*—Stephen E. Reiter

[57] ABSTRACT

Novel compositions are disclosed consisting essentially of aldehydes of the structure R—CHO (wherein R is a $C_8$–$C_{30}$ carbon radical) and about 0.1 to about 5 parts by weight of a triarylphosphine per 100 parts of aldehyde. In addition, a process for the recovery of essentially pure high boiling aldehyde by fractional distillation is provided wherein about 0.1 to about 5 parts by weight of a triarylphosphine per 100 parts of high boiling aldehyde is added to the aldehyde prior to distillation. Further, process for improving the high temperature storage stability of high boiling aldehydes is provided, which comprises adding about 0.1 to about 5 parts by weight of a triarylphosphine per 100 parts high boiling aldehyde to the aldehyde.

18 Claims, No Drawings

NOVEL ALDEHYDE-PHOSPHINE COMPOSITIONS AND USES THEREFOR

BACKGROUND

This invention relates to novel aldehyde-phosphine compositions. In another aspect, this invention relates to the recovery of purified aldehyde by distillation. In yet another aspect, this invention relates to stabilization of aldehydes with respect to decomposition when subjected to high temperature conditions.

Many aldehydes are known to undergo condensation reactions when subjected to elevated temperatures for prolonged periods of time. Thus, when it is attempted to purify aldehydes by distillation, significant amounts of aldehyde product can be lost due to formation of high molecular weight condensation products as a result of condensation reactions which occur in the distillation kettle during the distillation process. In addition, when it is attempted to purify aldehydes by distillation in the presence of alcohols of the same or similar chain lengths, co-distillation of such alcohols along with the desired aldehyde product can be a problem. Moreover, when aldehydes are subjected to storage at elevated temperatures, substantial quantities of aldehyde can be lost due to the occurrence of irreversible intermolecular reactions.

OBJECTS OF THE INVENTION

An object of the invention, therefore, is a process for the distillation of aldehydes wherein formation of high molecular weight condensation products is minimized.

Another object of the invention is aldehyde compositions which are stable under high temperature storage conditions.

These and other objects of the invention will become apparent from the disclosure and claims provided herein.

STATEMENT OF THE INVENTION

In accordance with the present invention, I have discovered that the recovery of adlehydes by distillation is improved by the addition of small amounts of triarlyphosphines to the distillation kettle. Decomposition of desired aldehyde product is reduced and, surprisingly, codistillation of alcohols which are hydroxy analogues of the product aldehyde is minimized.

In accordance with another embodiment of the invention, I have discovered novel aldehyde compositions with high temperature storage stability. Thus, the storage stability of aldehydes with respect to long term exposure of elevated temperatures can be dramatically improved by addition of small amounts of triarylphosphine to the aldehyde.

DETAILED DESCRIPTION OF THE INVENTION

In accordance with the present invention, there is provided a novel composition of matter consisting essentially of an aldehyde having the structure R—CHO, wherein R is a $C_8$–$C_{30}$ carbon radical and about 0.1 to about 5 parts by weight of a triarylphosphine per 100 parts of aldehyde.

In accordance with another embodiment of the present invention, a process for the recovery of essentially pure high boiling aldehydes from impure high boiling compositions by distillation is provided. High boiling aldehydes have the general structure R—CHO, wherein R is a $C_8$–$C_{30}$ carbon radical. By adding about 0.1 to about 5 parts by weight of a triarylphosphine per 100 parts of impure high boiling adlehyde to the impure aldehyde prior to distillation, improved recovery of aldehyde and reduced codistillation of alcohol impurities along with the desired aldehyde results.

In accordance with yet another embodiment of the present invention, a process for improving the high temperature storage stability of high boiling aldehydes having the structure R—CHO, wherein R is a $C_8$–$C_{30}$ carbon radical is provided. By adding 0.1 to about 5 parts by weight of a triarylphosphine per 100 parts of high boiling aldehyde to the aldehyde, the amount of aldehyde converted to high molecular weight condensation products when exposed to high temperature is dramatically reduced.

Aldehydes contemplated to be useful in the practice of the present invention can be defined broadly by the structure R—CHO, wherein R is a $C_8$–$C_{30}$ carbon radical. Preferably, R is a $C_8$–$C_{30}$ non-conjugated mono-unsaturated hydrocarbyl radical having the following structure:

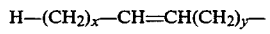

$$H-(CH_2)_x-CH=CH(CH_2)_y-$$

wherein x is 0-27, inclusive and y is 1-28, inclusive, because such compounds are particularly prone to decomposition when subjected to high temperature conditions, such as, for example, high temperature storage, or prolonged distillation conditions. Thus, preferred aldehydes will have the following structure:

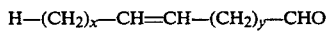

$$H-(CH_2)_x-CH=CH-(CH_2)_y-CHO$$

Most preferably, x is 0-10, inclusive and y is 3-12, inclusive.

Triarylphosphines contemplated to be useful in the practice of the present invention can be defined broadly by the structure $(Ar)_3P$, wherein each Ar is independently a $C_6$–$C_{12}$ aryl or alkyl-substituted aryl group. Exemplary compounds which conform to this structure include triphenylphosphine, tritolylphosphine, trixylylphosphine, trinaphthylphosphine, phenylditolylphosphine, diphenylnapththylphosphine and the like and mixtures of any two or more thereof. Triphenylphosphine is the presently preferred triarylphosphine for use in the practice of the present invention because of its ready availability, relatively low cost, and proven effectiveness in the desired applications.

The ratios of triarylphosphine to adlehyde contemplated to be within the scope of the present invention are broadly about 0.1 to about 5 parts by weight of triarylphosphine per 100 parts of aldehyde. Preferably, about 0.3 to about 2 parts by weight of triarylphosphine per 100 parts aldehyde will be employed. Most preferably, for most efficient use of the added triarylphosphine and effective stabilization of the aldehyde, about 0.5 to about 1 part by weight of the triarylphosphine per 100 parts aldehyde will be employed.

In the purification of aldehydes by fractional distillation, a frequent problem is the loss of substantial quantities of aldehyde due to intermolecular condensations of aldehyde to give high molecular weight condensation products. In addition, depending on the source of the aldehyde to be purified, impurities which are difficult to remove by distillation may also be present. For example, when aldehyde is prepared by the oxidation of a halide analogous to the desired aldehyde, an impurity frequently formed in significant quantities is an alcohol analogous to the desired aldehyde, i.e., an alcohol having the same number of carbon atoms as the desired aldehyde. Such analogous alcohols are very difficult to separate from the desired aldehyde by distillation and yet it is desirable to recover aldehyde with as little contaminating alcohol as possible, i.e., less than about 1%, for certain applications, such as for example, as synthetic pheromones. In accordance with a particular embodiment of the present invention, I have discovered that the addition of about 0.1 to about 5 parts by weight of a triarylphosphine per 100 parts of aldehyde greatly improves the recovery of aldehyde upon distillation. In addition, the amount of any impurity alcohol analogous to the aldehyde which codistills with the aldehyde product is greatly reduced.

While those of skill in the art can readily determine suitable conditions for the fractional distillation of high boiling aldehydes, it is preferred that distillation be carried out under reduced pressure so that the heat necessarily provided to the distillation kettle in order to cause fractionation can be minimized. In order to provide additional guidance, the following values are suggested:

|  | Pot Temperature, °C. | Pressure, mm Hg |
|---|---|---|
| Broad | 80-280 | 0.05-300 |
| Intermediate | 100-250 | 0.1-200 |
| Preferred | 120-200 | 0.1-10 |

In accordance with yet another embodiment of the invention, I have discovered that the storage stability of high boiling aldehydes when subjected to elevated temperatures for substantial periods of time can be greatly improved by the addition to the aldehyde of 0.1 up to about 5 parts by weight of triarylphosphine per 100 parts aldehyde. The novel aldehyde-triarylphosphine composition produced thereby is substantially more stable to formation of aldehyde condensation products compared to aldehyde similarly treated in the absence of triarylphosphine. Thus, the ability of aldehydes as defined above, to withstand high temperature storage (i.e., greater than room temperature) for substantial periods of time (i.e., greater than 1 hour) is greatly improved upon addition thereto of triarylphosphines. The benefits of the inventive process are especially visible where formulations including high boiling aldehydes are subjected to temperatures in excess of about 100° C. for times in excess of several hours. Such conditions may be encountered, for example, in less than favorable storage facilities or during the preparation of formulations for later use.

A further understanding of the present invention and its advantages will be provided by reference to the following non limiting examples.

EXAMPLE I

The Effect of Triphenylphosphine on Aldehyde Distillation a. Control

Run 1: Crude Z-11-hexadecenal (250 g), which was shown by GLC analysis to contain about:
68% aldehyde,
8% alcohol, and
24% other material,
was distilled through a 1-inch by 24-inch Goodloe packed column at about 0.3 mm Hg. Approximately 155 g of distillate was collected overheat at 128°-143° C., of which about 127 g (about 51% recovery) was Z-11-hexadecenal containing 1.4% alcohol.

b. Invention

Run 2: Another 250 g portion of crude Z-11-hexadecenal was distilled as above, except 2.5 g of triphenylphosphine was added to the distillation pot before distillation was started. Under similar conditions (0.3 mm Hg, overhead temperature of about 128°-143° C.), about 144 g of distillate was collected overhead, of which about 115 g (46% recovery) was Z-11-hexadecenal containing only 0.4% hexadecenol.

Run 3: Yet another 250 g portion of crude Z-11-hexadecenal was purified by distillation, this time with 1 g of added triophenylphosphine. About 152 g of distillate was collected overhead, of which about 126 g (about 50% recovery) was Z-11-hexadecenal containing only 0.2% hexadecenol.

Analyses of total distillation overhead and a representative heart cut for each of these distillations are summarized in Table I for ease of comparison. It is readily seen that the presence of very small amounts of triphenylphosphine greatly reduces the amount of alcohol impurity which codistills with the aldehyde product.

TABLE I

| Run | Crude Z-11-hexadecenal, g | Ph₃P, g | grams recovered | GLC ANALYSIS, % | | | |
|---|---|---|---|---|---|---|---|
| | | | | Total Overhead | | Heart Cut | |
| | | | | aldehyde | alcohol | aldehyde | alcohol |
| Feed | — | — | — | 68 | 8 | — | — |
| 1 (Control) | 250 | 0 | 155 | 82 | 1.4 | 98 | 1.0 |
| 2 (Invention) | 250 | 2.5 | 144 | 80 | 0.4 | 97 | 0.3 |
| 3 (Invention) | 250 | 1 | 152 | 83 | 0.2 | 98 | 0.2 |

EXAMPLE II

Thermal Stabilization of Aldehydes with Triphenylphosphine

One hundred grams of Z-11-hexadecenal was mixed with 25 grams of dibutyl phthalate (GLC internal standard) and heated in a nitrogen atmosphere at about 170° C. for 8 hours. GLC analysis indicated the formation of about 24% heavy materials.

The heat treatment procedure was repeated with several 100 g aliquots of Z-11-hexadecenal containing dibutyl phthalate as internal standard and small amounts of various additives. Results are summarized in Table II.

TABLE II

| Run | Additive, g | Treatment Conditions Temp. °C. | Time, h | % Heavy Material Formed |
|---|---|---|---|---|
| 1 | none | 170 | 8 | 24 |
| 2 | nicotinamide, 0.5 | 170 | 8 | 29 |
| 3 | o-aminophenol, 0.8 | 170 | 4 | 36 |
| 4 | t-butylcatechol, 0.25 | 170 | 8 | 18 |
| 5 | triphenylphosphine, 0.5 | 170 | 8 | 9 |

These results demonstrate that a triarylphosphine such as triphenylphosphine is an effective additive for the protection of aldehydes such as Z-11-hexadecenal from thermal degradation upon long term exposure to elevated temperatures. Less than one-half the amount of high molecular weight condensation products are formed when small amounts of triphenylphosphine are added to Z-11-hexadecenal which is heated to about 170° C. for 8 hours.

The examples have been provided merely to illustrate the practice of my invention and should not be read so as to limit the scope of my invention or the appended claims in any way. Reasonable variations and modifications, not departing from the essence and spirit of my invention, are contemplated to be within the scope of patent protection desired and sought.

That which is claimed:

1. A novel composition of matter consisting essentially of:
   (i) an aldehyde having the structure

R—CHO wherein R is a $C_8$–$C_{30}$ carbon radical, and
   (ii) 0.1–5 parts by weight of triarylphosphine per 100 parts of aldehyde, wherein the triarylphosphine has the structure:

$(Ar)_3P$ wherein each Ar is independently a $C_6$–$C_{12}$ aryl or alkyl-substituted aryl group.

2. A composition in accordance with claim 1 wherein R is a non-conjugated mono-unsaturated hydrocarbyl radical such that said aldehyde has the structure:

H—$(CH_2)_x$—CH=CH—$(CH_2)_y$—CHO wherein x is 0–27, inclusive and y is 1–28, inclusive.

3. A composition in accordance with claim 2 wherein x is 0–10, inclusive and y is 3–12, inclusive.

4. A composition in accordance with claim 2 wherein x is 4 and y is 9.

5. A composition in accordance with claim 1 wherein said triarylphosphine is triphenylphosphine.

6. A composition in accordance with claim 4 wherein said triarylphosphine is triphenylphosphine.

7. In a process for the recovery of essentially pure high boiling aldehyde from high boiling aldehyde-alcohol mixtures by distillation, wherein said high boiling aldehyde has the structure R—CHO and wherein R is a $C_8$–$C_{30}$ carbon radical, the improvement comprising adding 0.1 to 5 parts by weight of a triarylphosphine per 100 parts of high boiling aldehyde-alcohol mixture to the aldehyde-alcohol mixture prior to distillation, wherein the triaryl phosphine has the structure:

$(Ar)_3P$ wherein each Ar is independently a $C_6$–$C_{12}$ aryl or alkyl-substituted aryl group.

8. A process in accordance with claim 7 wherein R is a non-conjugated mono-unsaturated hydrocarbyl radical such that said aldehyde has the structure:

H—$(CH_2)_x$—CH=CH—$(CH_2)_y$—CHO wherein x is 0–27, inclusive and y is 1–28, inclusive.

9. A process in accordance with claim 8 wherein x is 0–10, inclusive and y is 3–12, inclusive.

10. A process in accordance with claim 8 wherein x is 4 and y is 9.

11. A process in accordance with claim 7 wherein said triarylphosphine is triphenylphosphine.

12. A process in accordance with claim 10 wherein said triarylphoshpine is triphenylphoshpine.

13. A process for improving the high temperature storage stability of high boiling aldehydes having the structure R—CHO, wherein R is a $C_8$–$C_{30}$ carbon radical, said process comprising adding 0.1–5 parts by weight of a triarylphosphine per 100 parts high boiling aldehyde to the aldehyde, wherein said triarylphosphine has the structure $(Ar)_3P$, and wherein each Ar is independently a $C_6$–$C_{12}$ aryl or alkyl-substituted aryl group.

14. A process in accordance with claim 13 wherein R is a non-conjugated mono-unsaturated hydrocarbyl radical such that said aldehyde has the structure:

H—$(CH_2)_x$—CH=CH—$(CH_2)_y$—CHO wherein x is 0–27, inclusive and y is 1–28, inclusive.

15. A process in accordance with claim 14 wherein x is 0–10, inclusive and y is 3–12, inclusive.

16. A process in accordance with claim 14 wherein x is 4 and y is 9.

17. A process in accordance with claim 13 wherein said triarylphosphine is triphenylphosphine.

18. A process in accordance with claim 16 wherein said triarylphosphine is triphenylphosphine.

* * * * *